United States Patent
Nagarajan et al.

(10) Patent No.: US 6,963,403 B2
(45) Date of Patent: Nov. 8, 2005

(54) METHOD FOR DETERMINING THE REFLECTANCE PROFILE OF MATERIALS

(75) Inventors: Ramakrishnan Nagarajan, New Delhi (IN); Sathya Prakash Varma, New Delhi (IN); Devinder Gupta, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 217 days.

(21) Appl. No.: 10/341,595

(22) Filed: Jan. 14, 2003

(65) Prior Publication Data

US 2003/0151747 A1 Aug. 14, 2003

Related U.S. Application Data

(60) Provisional application No. 60/347,878, filed on Jan. 15, 2002.

(51) Int. Cl.⁷ ................................................ G01N 21/55
(52) U.S. Cl. ....................................................... 356/445
(58) Field of Search .................. 356/445–448

(56) References Cited

U.S. PATENT DOCUMENTS

| | | | | |
|---|---|---|---|---|
| 4,618,541 A | * | 10/1986 | Forouhi et al. | 428/688 |
| 5,132,922 A | * | 7/1992 | Khan et al. | 356/43 |
| 5,597,868 A | * | 1/1997 | Kunz | 525/154 |

OTHER PUBLICATIONS

Simmons, E.L., "Diffuse reflectance spectroscopy: a comparison of the theories", Applied Optics, vol. 14, No. 6, Jun. 1975, pp. 1380–1386.*

Garbuny, Max, "Optical Physics", Academic Press, New York, New York, 1965.*

* cited by examiner

Primary Examiner—Richard A. Rosenberger
(74) Attorney, Agent, or Firm—Foley & Lardner LLP

(57) ABSTRACT

The present invention relates to a method for determining the reflectance profile of materials and more particularly, the present invention relates to a method for calculating specular and diffuse reflectance and hence, the emittance of materials at ambient temperatures.

34 Claims, 5 Drawing Sheets

Figure 1A:
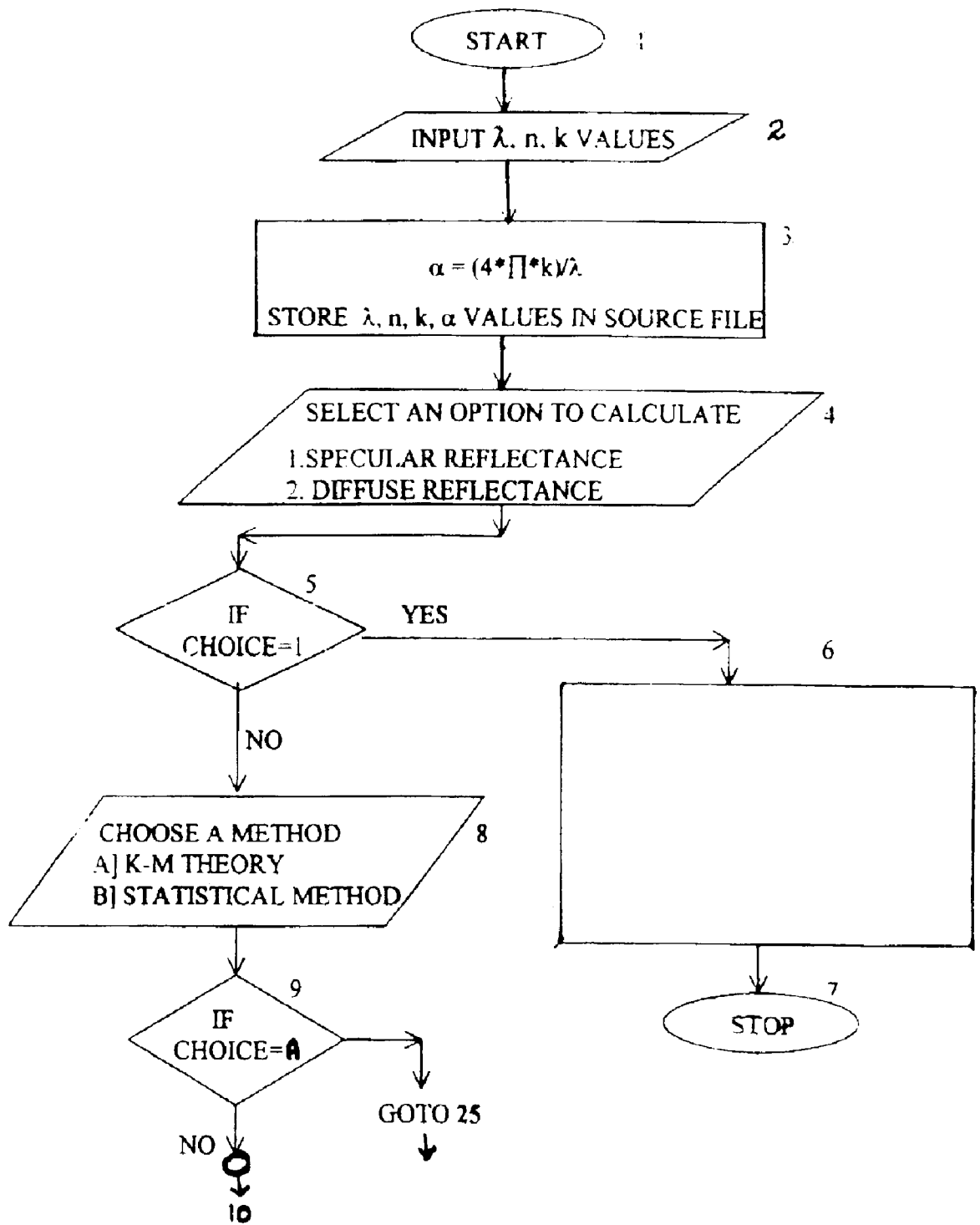
Figure 1B:
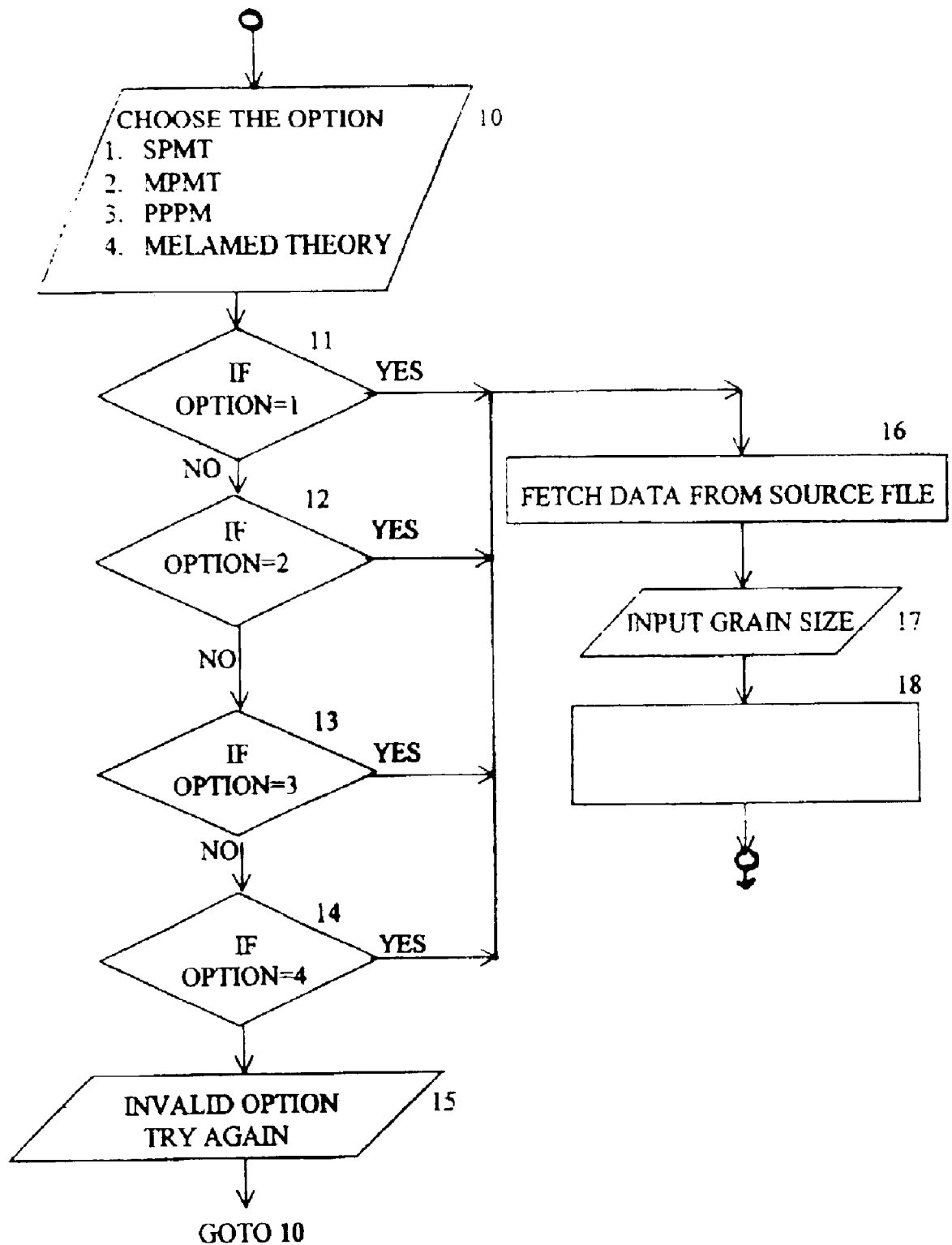
Figure 1C:
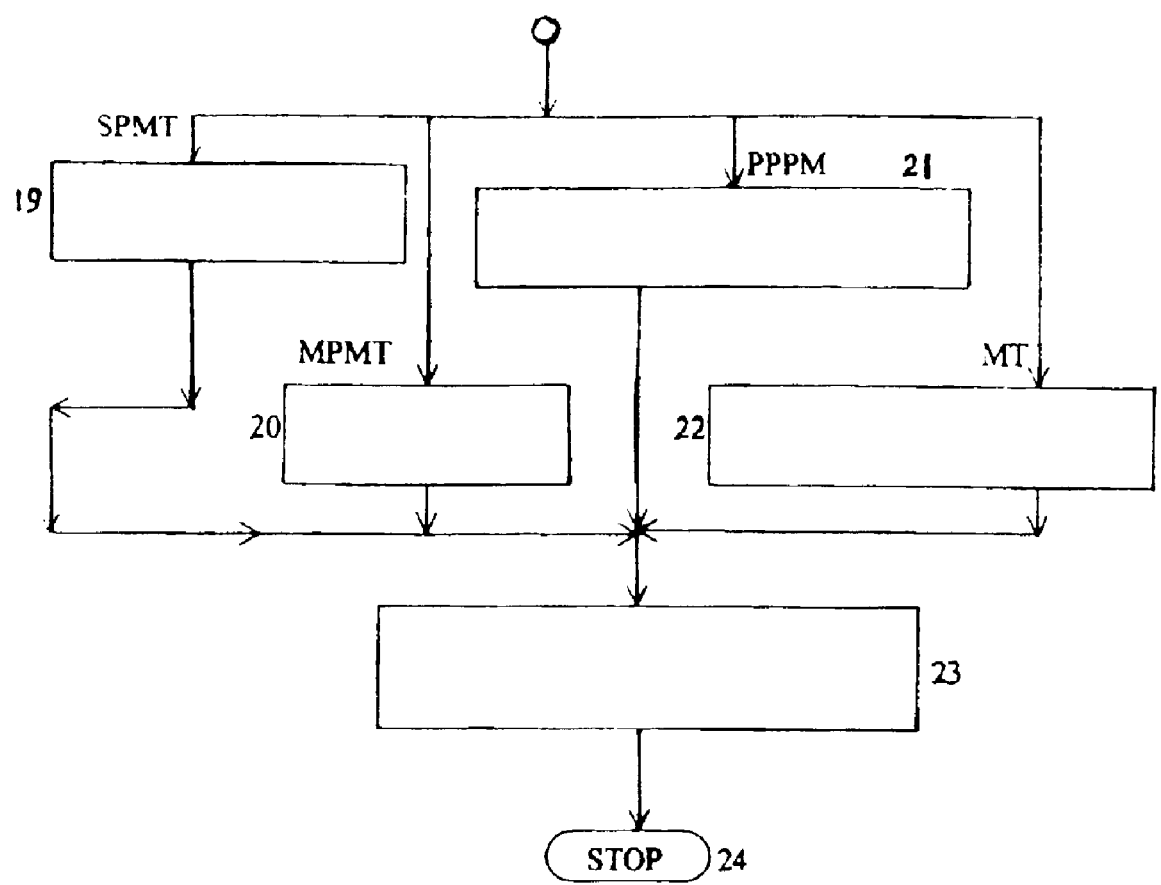
Figure 1D:
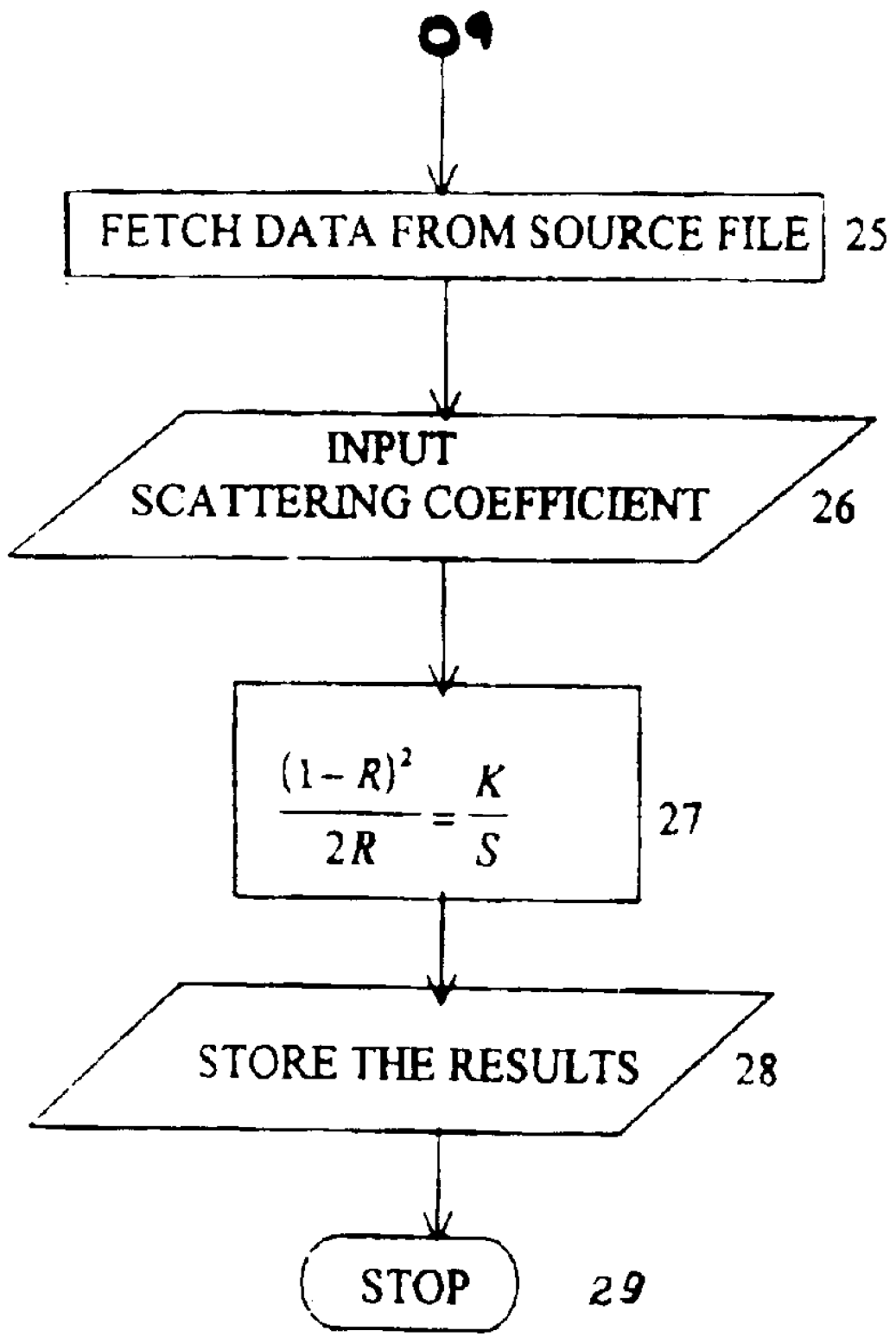

Specular reflectance values of both surfaces polished germanium at an incident angle 10°.

a) Calculated (xxx) and b) Experimental (+++) values of specular reflectance.

METHOD FOR DETERMINING THE REFLECTANCE PROFILE OF MATERIALS

REFERENCE TO RELATED APPLICATIONS

This application claims benefit from the Provisional Application No. 60/347,878 filed Jan. 15, 2002.

FIELD OF INVENTION

The present invention relates to a method for determining the reflectance profile of materials and more particularly, the present invention relates to a method for simultaneously determining diffuse reflectance and specular reflectance of materials at ambient temperatures.

BACKGROUND AND PRIOR ART DESCRIPTION

In the area of energy conservation and the processes where heat transfer mechanism plays an important role, emittance of the material is an important parameter, which should be known accurately and precisely for its optimization. The value of the emittance of a material at any temperature is, generally, derived from the ratio of the irradiance of the material and that of the blackbody maintained at that temperature of the material. In the mid-infrared region, for the determination of the emittance of a material at room ambient this method is not successful because of low signal to noise ratio.

The determination of diffuse reflectance is important because of its day to day applications in terms of determining
1. Quality of fruits/vegetables.
2. Fat content in milk.

The measurement of diffuse reflectance can also be used in studying:
1. Influence of computer key boards on visual functions and
2. Quantification of brain endema.

Moreover, diffuse reflectance study is the effective tool for the following fields:
1. Remote sensing: by monitoring diffusely reflected radiation from remote objects/targets.
2. Forensic Science: by maintaining the data bank on automobile paint, etc.,
3. Energy conservation material analysis: Developmental work on designing new materials.
4. Pollution monitoring: by monitoring the industrial & automobile exhaust for the pollution.
5. Fire Proof material analysis: developmental work on uniforms for the fire fighting units.
6. Military Application: Applications like creating the signature of the target for passive IR systems.

All these things show the importance of the work to be carried out.

The Applicants have found that if the amount of energy of specular reflectance ($R_s$) and diffuse reflectance ($R_d$) and also the amount of energy of regular transmittance ($T_s$) and diffuse transmittance ($T_d$) are determined, the total amount of energy absorbed may be easily derived from the following equation:

$$\text{Absorptance} = 1 - [R_s + R_d + T_s + T_d]$$

Here, ($R_s + R_d$) is the reflectance value and similarly ($T_s + T_d$) is the transmittance value. According to Kirchhoff's law, the absorption of a material is equal to its emittance. Hence the above relation can be written as:

$$\text{Emittance} = 1 - [R_s + R_d + T_s + T_d]$$

Since this relation is more suitable for the spectral region of 2.5 µm to 15 µm, it seems to be a method for precise determination of absorptance or emittance of materials at ambient temperature. For opaque coatings, the contributions from diffuse and regular components of transmittance are zero and for opaque coatings on a rough surface, the contribution from regular reflectance is also zero. Thus for a case of opaque coating on a rough surface, the diffuse reflectance will only contribute to emittance.

Though, theoretically it seems simple but experimentally the determination of diffuse reflectance/transmittance would have been possible only after the invention and availability of efficient diffuse coating material, Fourier Transform Infrared Spectrophotometer and the sensitive, fast, low noise detectors.

References may be made to the article entitled "Diffuse reflectance spectroscopy: a comparison of the theories" by E. L. Simmons, Applied Optics vol. 14 (1975), wherein all the existing models are discussed in a detailed way to handle the diffuse reflectance problem. Even though details about the principle and intricacies are described, no computational procedure is reported.

Another reference may be made to an article titled "Optical properties of powders. Part I. Optical absorption coefficients and absolute value of diffuse reflectance. Part II. Properties of luminescent powders" by N. T. Melamed, Journal of Applied Physics vol. 34 (1963) gives an account of the theory developed by him to solve the diffuse reflectance problem. There also no specific computation is discussed.

Yet another reference may be made to an article titled "An Article on Optics of Paint Layers" by Kubelka-Munk. The article gives an idea about the differential equation method. It discusses the theoretical treatment of the optics of coatings.

Still another reference may be made to an article titled "Measurement of total reflectance, transmittance and emissivity over the thermal IR spectrum" by F. J. J. Clarke and J. A. Larkin. The article discusses about the diffuse reflectometer/transmissometer that can determine the diffuse reflectance/transmittance of any type of sample.

OBJECTS OF THE INVENTION

The main object of the present invention is to provide a method for determining reflectance profile of materials.

Another object of the present invention is to provide a method for determining as a whole the specular reflectance and diffuse reflectance of materials.

Still another object of the present invention is to provide a method for determining reflectance of a material using specular and diffuse reflectance.

Yet another object of the present invention is to design new materials by means of theoretical characterization.

One more object of the present invention is to characterize the materials based on the reflectance profile.

A further object of the present invention is to provide software for developing a new material by studying various theoretical compositions for their reflectance value and experimenting their combination.

BRIEF DESCRIPTION OF THE ACCOMPANYING DRAWINGS

In the drawings accompanying the specification,

FIGS. 1(a) to 1(d) show a basic flow chart representing the method of the present invention.

Figure 2:
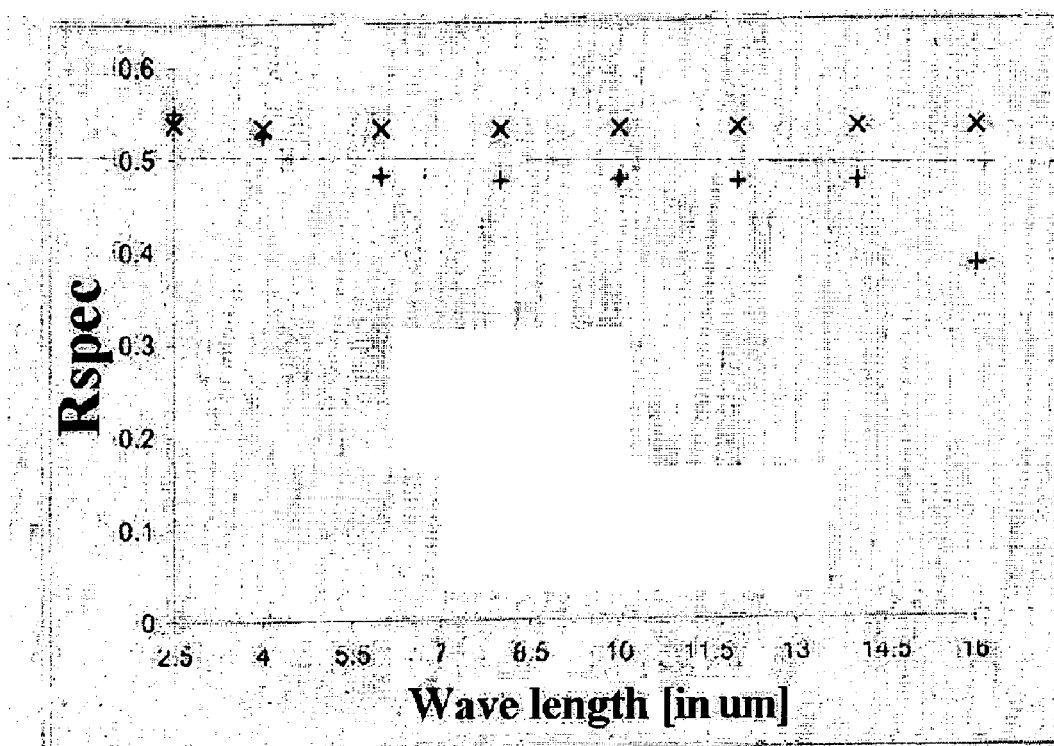

FIG. 2 shows the agreement of experimental results with the theoretical calculation.

SUMMARY OF INVENTION

The present invention relates to a method for determining the reflectance profile of materials and more particularly, the present invention relates to a method for simultaneously determining diffuse reflectance and specular reflectance of materials at ambient temperatures.

DESCRIPTION OF THE INVENTION

Accordingly, the present invention provides a method for calculating specular and diffuse reflectance and hence, the emittance of materials, the said method comprising the steps of:
(a) obtaining the input parameters wavelength ($\lambda$), refractive index (n), extinction coefficient (k) and angle of incidence ($\theta$) from the user;
(b) calculating absorption coefficient ($\alpha$);
(c) prompting the user to choose between calculation of specular reflectance and calculation of diffuse reflectance;
(d) if specular reflectance is selected by the user, calculating u, v, parallel component of specular reflectance (Rs), perpendicular component of specular reflectance (Rp) and calculating the mean of the parallel and the perpendicular components thus obtained above to obtain the specular reflectance;
(e) if diffuse reflectance is selected, prompting the user to select between K-M Method and statistical method;
(f) if K-M method is selected by the user, obtaining scattering coefficient (S) from the user and calculating diffuse reflectance;
(g) if statistical method is selected, obtaining grain size from the user and calculating external reflection coefficient ($m_e$) and internal reflection coefficient ($m_i$);
(h) calculating 'r' and 't' using any one of the following four statistical methods, and
  (i) Simplified particle model theory,
  (ii) Modified particle model theory,
  (iii) Plane parallel plate theory, and
  (iv) Melamed theory
(i) calculating the diffuse reflectance statistically using 'r' and 't' thus obtained in step (h).

In an embodiment of the present invention wherein in step (b), the absorption coefficient ($\alpha$) is defined as: $\alpha=(4\pi k)/\lambda$ In another embodiment of the present invention wherein in step (c), if the user selection is neither for specular nor for diffuse reflectance, then the user is asked to make the proper choice or to terminate.

In yet another embodiment of the present invention wherein in step (d), 'u' is defined as:

$$u^2 = \frac{\{(n^2 - k^2 - \sin^2\theta) + \sqrt{[(n^2 - k^2 - \sin^2\theta)^2 + ]4n^2k^2}\}}{2}$$

In still another embodiment of the present invention wherein in step (d), 'v' is defined as:

$$v^2 = \frac{\{(k^2 - n^2 + \sin^2\theta) + \sqrt{[(n^2 - k^2 - \sin^2\theta)^2 + ]4n^2k^2}\}}{2}$$

In one more embodiment of the present invention wherein in step (d), the parallel component of specular reflectance (Rs) is defined as:

$$R_s = \frac{[(\cos\theta - u)^2 + v^2]}{[(\cos\theta + u)^2 + v^2]}$$

In one another embodiment of the present invention wherein in step (d), the perpendicular component of specular reflectance (Rp) is defined as:

$$R_p = \frac{[(\{n^2 - k^2\}\cos\theta - u)^2 + (2nk\cos\theta - v)^2]}{[(\{n^2 - k^2\}\cos\theta + u)^2 + (2nk\cos\theta + v)^2]}$$

In a further embodiment of the present invention wherein in step (d), the specular reflectance (R) is defined as:

$$R=(R_s+R_p)/2$$

In an embodiment of the present invention, wherein after obtaining the specular reflectance in step (d), the user is provided with an opportunity to calculate the diffuse reflectance or to terminate the program.

In another embodiment of the present invention wherein in step (e), if the user selection is neither for K-M method nor for statistical method, then the user is asked to make a proper choice or to terminate.

In yet another embodiment of the present invention wherein in step (f), diffuse reflectance (R) is defined by K-M method as:

$$\frac{(1 - R)^2}{2R} = \frac{K}{S}$$

wherein K stands for absorption coefficient.

In still another embodiment of the present invention, wherein after obtaining the diffuse reflectance in step (f) by the K-M method, the user is provided with an opportunity to calculate the diffuse reflectance by the statistical method or to calculate the specular reflectance or to terminate the program.

In one more embodiment of the present invention, wherein if the user doesn't make a proper choice in step (h), he is asked to make a proper choice or to terminate.

In one another embodiment of the present invention wherein in step (g), according to the statistical method, external reflection coefficient ($m_e$) is defined as:

$$m_e = \frac{1}{2}\left(\frac{n_2\cos\theta - [n^2 - \sin^2\theta]^{1/2}}{n_2\cos\theta + [n^2 - \sin^2\theta]^{1/2}}\right)^2 + \frac{1}{2}\left(\frac{\cos\theta - [n^2 - \sin^2\theta]^{1/2}}{\cos\theta + [n^2 - \sin^2\theta]^{1/2}}\right)^2$$

In a further embodiment of the present invention wherein in step (g), according to the statistical method, internal reflection coefficient ($m_i$) is defined as:

$$m_e = 1 - \left[\frac{(1 - m_e)}{n^2}\right]$$

In an embodiment of the present invention wherein in step (h), Simplified particle model theory defines 'r' and 't' as:

$$r = t = \left(\frac{1-A}{2}\right)$$

wherein, Absorbance $A = \left[\frac{(1-m_e)(1-T)}{(1-m_iT)}\right]$ wherein, $T e^{-2\alpha d/3}$ In another embodiment of the present invention wherein in step (h), Modified particle model theory defines 'r' and 't' as:

$$r = \left(\frac{3m_e}{4}\right) + \frac{T}{2}[(1-m_e)(1-m_i)] \times \left\{\frac{1}{(1-m_iT)} - \frac{(1-m_i/2)(1-m_e/2)}{1+m_iT/2}\right\}$$

$$t = \left(\frac{m_e}{4}\right) + \frac{T}{2}[(1-m_e)(1-m_i)] \times \left\{\frac{1}{(1-m_iT)} + \frac{(1-m_i/2)(1-m_e/2)}{1+m_iT/2}\right\}$$

In yet another embodiment of the present invention wherein in step (h), Parallel plane model defines 'r' and 't' as:

$$r = r_0 + \left[\frac{(1-r_0)^2 r_0 e^{-\alpha d}}{1 - r_0^2 e^{-2\alpha d}}\right]$$

and $$t = \left[\frac{(1-r_0)^2 e^{-\alpha d}}{1 - r_0^2 e^{-2\alpha d}}\right]$$

wherein $$r_0 = \left(\frac{1-n}{1+n}\right)^2$$

In still another embodiment of the present invention wherein in step (h), Melamed theory defines 'r' and 't' as:

$$r = m_e + \frac{1}{2}\left\{\frac{(1-m_e)(1-m_i)M}{1-m_iM}\right\}$$

and $$t = \frac{1}{2}\left\{\frac{(1-m_e)(1-m_i)M}{1-m_iM}\right\}$$

wherein $$M = \frac{2}{(\alpha d)^2}[1 - (\alpha d + 1)e^{-\alpha d}]$$

In one more embodiment of the present invention wherein in step (i), diffuse reflectance (R) is defined by the statistical method as:

$$R = \frac{(1 + r^2 - t^2) + [(1 + r^2 - t^2)^2 - 4r^2]^{1/2}}{2r}$$

In one another embodiment of the present invention wherein after obtaining the diffuse reflectance in step (i) by the statistical method, the user is provided with an opportunity to calculate the diffuse reflectance by the K-M method or to calculate the specular reflectance or to terminate the program.

In a further embodiment of the present invention if the user doesn't make a proper choice at any stage, he is asked to make a proper choice or to terminate.

In an embodiment of the present invention, the parameters obtained from the user and those calculated are stored in a file.

In another embodiment of the present invention, the file is a new file or an already existing file.

In yet another embodiment of the present invention, the method is used in infrared region.

In still another embodiment of the present invention, the method is used in the wavelength range of 0.8 µm to 1000 µm.

In one more embodiment of the present invention, the said method is used in visible region.

In an embodiment of the present invention, the method is used in the wavelength range of 400 nm to 800 nm.

In another embodiment of the present invention, the method is used in UV region.

In yet another embodiment of the present invention, the method is used in the wavelength range of 200 nm to 400 nm.

In still another embodiment of the present invention, the method is used for calculating specular and diffuse reflectance of solids selected from the group comprising of metals, non-metals, conductors, semiconductors, insulators and dielectrics and liquids selected from the group comprising of organic and inorganic liquids.

In one more embodiment of the present invention the agreement between experimental and computed specular reflectance values is ±5%.

In another embodiment the method is used for optical characterization of new materials.

In another embodiment the method is used for development of required materials for fire proof materials.

In still another embodiment the method is used for development of required materials for energy saving process.

According to another embodiment the method is used for development of required materials for thermal insulation.

The present invention is further described in the following paragraphs and the examples which are given by way of illustration and hence, should not be construed to limit the scope of the present invention in any manner.

Theory

The polished surfaces reflect the radiation following the laws of reflection. i.e., angle of incidence is equal to angle of reflection and incident beam, reflected beam and the normal to the surface all lie in the same plane. In practical life, all the surfaces are not polish to contribute specular reflectance and hence an alternative technique is to be devised to study the reflectance of such materials. These surfaces may specularly reflect partially or even negligibly but mostly scatter or diffusely reflect the radiation. This is measured in a laboratory by an Integrating Sphere, which has diffusely reflecting surface for the spectral region of interest. The material used for the diffusely reflecting surface varies with the spectral region of interest. In visible and UV region the material for the diffusely reflecting surface are very well established but in the spectral region of 2.5 µm to 15 µm, it is still in the investigation stage. Most of the materials and surfaces have not been characterized so far for their hemispherical reflectance and hemispherical transmittance in 2.5 µm to 15 µm spectral region. Hence the study of these parameters is necessary.

Specular reflectance study is simpler as it obeys Fresnel's law of reflection, but the diffuse part is quite complicated.

The specialty of diffuse reflectance/transmittance studies is that they do not require any sample preparation and surface finish. The materials as such in its usual form can be characterized by diffuse reflectance studies. Moreover the mapping by remote sensing enhances the significance of diffuse reflectance/transmittance measurements. Though efforts had been made to study diffuse reflectance in visible region, the work in the mid infrared spectral region: 2.5 $\mu$m to 15 $\mu$m is quite new and not many references are reported.

As per the already existing literature, there exist three methods, the integral equation method, differential equation method which is the generally known as Kubelka-Munk (K-M) theory and the statistical method. Out of these three, the first two treat the powdered sample as a continuous medium. In the statistical method there are two approaches. One assumes the powdered sample as a collection of uniformly sized rough surface particles of spherical shape and the other is considering the powdered sample as a collection of parallel plane layers whose thickness is the average diameter of the particles. Out of these three theories, only K-M theory & statistical approach are taken into account, because they are very widely used by many researchers.

Computer Software are for Reflectance Profile

The computer software is developed with the help of DOS based C language. So either DOS or Windows operating system is sufficient to run the program. This software deals with the computation of reflectance of materials in the mid-infrared region. It handles the calculation of both specular as well as diffuse reflectance. Diffuse reflectance study is extensively done for almost all the existing methods, which are suggested.

As mentioned already, through this software a theoretical analysis of reflectance/emittance of a material is possible. So, after analyzing a material theoretically, it is easy to decide whether it is to be experimented or not, which will reduce the cost of effect of sample preparation and analysis and time consumption as well.

FIGS. 1(a) to 1(d) show a basic flow chart representing the method of the present invention. FIGS. 1(a) to 1(d) are described in detail below. The method starts in step 1. Parameters like wavelength ($\lambda$), refractive index (n), extrinction coefficient (k) and angle of incidence ($\theta$) are obtained from the user in step 2. Absorption coefficient ($\alpha$) is calculated in step 3 as: $\alpha=(4\pi k)/\lambda$.

In steps 4, the user is asked to choose between calculation of specular reflectance and calculation of diffuse reflectance. The user's choice is checked in step 5. If the user chooses to calculate specular reflectance, steps 6 and 7 are followed. However, if the user chooses to calculate diffuse reflectance, steps 8 and onwards are followed.

As described above, steps 6 and 7 are performed if the user chooses to calculate specular reflectance. Specular reflectance experiments are done for materials like germanium, silicon, zinc sulphide. The agreement of experimental results with the theoritical calculation is shown in FIG. 2.

As the specular part has two components, called parallel and perpendicular components, the mean of these two serves R. To find out $R_s$ and $R_p$, u and v are the two terms necessary. So in step 6, u, v, $R_s$, $R_p$ are first calculated and they are used for calculating specular reflectance R using the following formulae:

$$R = (R_s + R_p)/2 \text{ where}$$

$$R_s = \frac{[(\cos\theta - u)^2 + v^2]}{[(\cos\theta + u)^2 + v^2]} \text{ and}$$

$$R_p = \frac{[(\{n^2 - k^2\}\cos\theta - u)^2 + (2nk\cos\theta - v)^2]}{[(\{n^2 - k^2\}\cos\theta + u)^2 + (2nk\cos\theta + v)^2]} \text{ where}$$

$$u^2 = \frac{\{(n^2 - k^2 - \sin^2\theta) + \sqrt{[(n^2 - k^2 - \sin^2\theta)^2 + ]4n^2k^2}\}}{2}$$

$$v^2 = \frac{\{(k^2 - n^2 + \sin^2\theta) + \sqrt{[(n^2 - k^2 - \sin^2\theta)^2 + ]4n^2k^2}\}}{2}$$

where n is the refractive index and k is the extinction coefficient of the material respectively and $\theta$ is the angle of incidence, which can be varied from 10° to 70°.

If the user chooses to calculate diffuse reflectance, he proceeds to step 8, wherein he is asked to choose a method by which he desires to calculate the diffuse reflectance. More particularly, the user is asked to choose between K-M theory and Statistical method for calculating the diffuse reflectance.

The user's choice is checked in step 9. If the user chooses to calculate diffuse reflectance by K-M method, steps 25 to 29 are followed. However, if the user chooses to calculate diffuse reflectance by statistical method, steps 10 to 24 are followed.

If the user chooses to calculate diffuse reflectance by K-M method, then in step 25, the input parameter absorption coefficient is obtained from the place where it is stored. In step 26, scattering coefficient is obtained from the user. In step 27, the diffuse reflectance R is calculated using the formula and the result thus obtained is stored.

$$\frac{(1-R)^2}{2R} = \frac{K}{S}$$

If the user chooses to calculate diffuse reflectance by statistical method, he proceeds to step 10, wherein he is further asked to choose a statistical method by which he desires to calculate the diffuse reflectance. More particularly, the user is asked to choose between Simplified particle model theory, Modified particle model theory, Plane parallel plate model and Melamed theory.

Steps 11 to 14 determine the user's choice and if the user has not made a proper choice, step 15 asks him to make a proper choice.

It should noted that steps 16 to 18 are performed for all user choice. In step 16, the input parameters refractive index (n), angle of incidence ($\theta$) and absorption coefficient ($\alpha$) are retrieved from the place where it is stored and grain size is obtained from the user in step 17.

In step 18, the external reflection coefficient ($m_e$) and the internal reflection coefficient ($m_i$) are determined as these two parameters are invariably used in all statistical methods. The external reflection coefficient ($m_e$) and the internal reflection coefficient ($m_i$) are defined as follows:

$$m_e = \frac{1}{2}\left(\frac{n_2\cos\theta - [n^2 - \sin^2\theta]^{1/2}}{n_2\cos\theta + [n^2 - \sin^2\theta]^{1/2}}\right)^2 + \frac{1}{2}\left(\frac{\cos\theta - [n^2 - \sin^2\theta]^{1/2}}{\cos\theta + [n^2 - \sin^2\theta]^{1/2}}\right)^2$$

and $$m_i = 1 - \left[\frac{(1 - m_e)}{n^2}\right]$$

To calculate the diffuse reflectance by the statistical method, 'r' and 't' are the two parameters required and 'r' and 't' is determined through simplified particle model theory, modified particle model theory, plane parallel plate model theory or Melamed theory.

If the user chooses to calculate 'r' and 't' using simplified particle model theory then step 19 is performed wherein 'r' and 't' are calculated as:

$$r = t = \left(\frac{1-A}{2}\right)$$

wherein, Absorbance $A = \left[\frac{(1-m_e)(1-T)}{(1-m_i T)}\right]$ wherein, $T = e^{-2\alpha d/3}$ If the user chooses to calculate 'r' and 't' using modified particle model theory then step 20 is performed wherein 'r' and 't' are calculated as:

$$r = \left(\frac{3m_e}{4}\right) + \frac{T}{2}[(1-m_e)(1-m_i)] \times \left\{\frac{1}{(1-m_i T)} - \frac{(1-m_i/2)(1-m_e/2)}{1+m_i T/2}\right\}$$

$$t = \left(\frac{m_e}{4}\right) + \frac{T}{2}[(1-m_e)(1-m_i)] \times \left\{\frac{1}{(1-m_i T)} + \frac{(1-m_i/2)(1-m_e/2)}{1+m_i T/2}\right\}$$

If the user chooses to calculate 'r' and 't' using parallel plane model then step 21 is performed wherein 'r' and 't' are calculated as:

$$r = r_0 + \left[\frac{(1-r_0)^2 r_0 e^{-\alpha d}}{1 - r_0^2 e^{-2\alpha d}}\right] \text{ and}$$

$$t = \left[\frac{(1-r_0)^2 e^{-\alpha d}}{1 - r_0^2 e^{-2\alpha d}}\right]$$

wherein $$r_0 = \left(\frac{1-n}{1+n}\right)^2$$

If the user chooses to calculate 'r' and 't' Melamed theory then step 22 is performed wherein 'r' and 't' are calculated as:

$$r = m_e + \frac{1}{2}\left\{\frac{(1-m_e)(1-m_i)M}{1-m_i M}\right\}$$

$$t = \frac{1}{2}\left\{\frac{(1-m_e)(1-m_i)M}{1-m_i M}\right\} \text{ wherein}$$

$$M = \frac{2}{(\alpha d)^2}[1 - (\alpha d + 1)e^{-\alpha d}]$$

After obtaining 'r' and 't' from any one of the four methods, the statistical method calculated the diffuse reflectance (R) in step 23 wherein diffuse reflectance (R) is defined as:

$$R = \frac{(1+r^2-t^2) + [(1+r^2-t^2)^2 - 4r^2]^{1/2}}{2r}$$

The diffuse reflectance thus obtained in step 23 is stored. Repeating all the above-said steps for another material or ending up the execution is to be decided by the user's requirement.

After completing the calculation, results are stored in the file as mentioned already. Further appending or terminating the program is left to the user.

Following examples are given for illustrative purposes only and should not be construed to limit the scope of invention

EXAMPLE 1

Energy Conservation: Material Analysis

The reliable prediction of energy gains & losses to and from structures such as buildings, green houses, space vehicles and industrial process plant is very important for energy conservation & control process. For this purpose, the method of the present invention is used to characterize new materials for developmental work.

EXAMPLE 2

Pollution Monitoring

Exhaust from industries as well as from automobiles is analyzed for their constituents by IR analyzer based on their diffuse reflectance spectra.

EXAMPLE 3

Field of Fireproof & Energy Conservation

In designing uniforms for the fire troop, requirement of feasible materials is always there. To make a better quality fireproof uniform material, diffuse reflectance studies are to be carried out on various compositions of materials. Out of all the possible compositions, the best or the better may be chosen for making fire proof uniforms.

EXAMPLE 4

Bio-applications

Brain edema analysis and impact of diffuse reflectance of computer keyboards on visual functions are a few of the leading areas in which studies are progressing.

EXAMPLE 5

Remote Sensing

Mapping of various lands and objects on earth for their details is possible using this method.

EXAMPLE 6

Forensic Scienc

In case of any accident or otherwise, to obtain the details of automobile such as model and its year of make.

What is claimed is:

1. A method for calculating the emittance of materials at ambient temperatures from specular and diffuse reflectance, comprising:

(a) obtaining input parameters of wavelength ($\lambda$), refractive index (n), extinction coefficient (k) and angle of incidence ($\theta$) from a user;

(b) calculating an absorption coefficient ($\alpha$) based on $\lambda$ and k;

(c) prompting the user to choose between calculation of specular reflectance and calculation of diffuse reflectance;

(d) if specular reflectance is selected by the user, calculating a parallel component of specular reflectance (Rs), perpendicular component of specular reflectance (Rp), and calculating the mean of the parallel and the perpendicular components to obtain the specular reflectance;

(e) if diffuse reflectance is selected, prompting the user to select between K-M Method and statistical method;

(f) if K-M method is selected by the user, obtaining scattering coefficient (S) from the user and calculating diffuse reflectance;

(g) if statistical method is selected, obtaining grain size from the user and calculating external reflection coefficient ($m_e$) and internal reflection coefficient ($m_i$);

(h) calculating the diffuse reflectance using any one of the following four statistical methods:
 (i) Simplified particle model theory,
 (ii) Modified particle model theory,
 (iii) Plane parallel plate theory, and
 (iv) Melamed theory; and (i) calculating the emittance based on the calculated specular and diffuse reflectance.

2. A method as claimed in claim 1, wherein in step (b), the absorption coefficient ($\alpha$) is defined as: $\alpha = (4\pi k)/\lambda$.

3. A method as claimed in claim 1, wherein in step (c), if the user selection is neither for specular nor for diffuse reflectance, then the user is asked to make the proper choice or to terminate.

4. A method as claimed in claim 1, wherein in step (d), the parallel component of specular reflectance (Rs) is defined as:

$$R_s = \frac{[(\cos\theta - u)^2 + v^2]}{[(\cos\theta + u)^2 + v^2]},$$

wherein 'u' is defined by:

$$u^2 = \frac{\{(n^2 - k^2 - \sin^2\theta) + \sqrt{[(n^2 - k^2 - \sin^2\theta)^2 + ]4n^2k^2}\}}{2}, \text{ and}$$

v' is defined by:

$$v^2 = \frac{\{(k^2 - n^2 + \sin^2\theta) + \sqrt{[(n^2 - k^2 - \sin^2\theta)^2 + ]4n^2k^2}\}}{2}.$$

5. A method as claimed in claim 1, wherein in step (d), the perpendicular component of specular reflectance (Rp) is defined as:

$$R_p = \frac{[(\{n^2 - k^2\}\cos\theta - u)^2 + (2nk\cos\theta - v)^2]}{[(\{n^2 - k^2\}\cos\theta + u)^2 + (2nk\cos\theta + v)^2]},$$

wherein 'u' is defined by:

$$u^2 = \frac{\{(n^2 - k^2 - \sin^2\theta) + \sqrt{[(n^2 - k^2 - \sin^2\theta)^2 + ]4n^2k^2}\}}{2}, \text{ and}$$

v' is defined by:

$$v^2 = \frac{\{(k^2 - n^2 + \sin^2\theta) + \sqrt{[(n^2 - k^2 - \sin^2\theta)^2 + ]4n^2k^2}\}}{2}.$$

6. A method as claimed in claim 1, wherein in step (d), the specular reflectance (R) is defined as:

$$R = (R_s + R_p)/2.$$

7. A method as claimed in claim 1, wherein after obtaining the specular reflectance in step (d), the user is provided with an opportunity to calculate the diffuse reflectance or to terminate the program.

8. A method as claimed in claim 1, wherein in step (e), if the user selection is neither for K-M method nor for statistical method, then the user is asked to make a proper choice or to terminate.

9. A method as claimed in claim 1, wherein in step (f), diffuse reflectance (R) is defined in the K-M method as:

$$\frac{(1-R)^2}{2R} = \frac{K}{S},$$

wherein K stands for absorption coefficient.

10. A method as claimed in claim 1, wherein after obtaining the diffuse reflectance in step (f) by the K-M method, the user is provided with an opportunity to calculate the diffuse reflectance by the statistical method or to calculate the specular reflectance or to terminate the program.

11. A method as claimed in claim 1, wherein if the user doesn't make a proper choice in step (h), he is asked to make a proper choice or to terminate.

12. A method as claimed in claim 1, wherein in step (g), according to the statistical method, the external reflection coefficient ($m_e$) is defined as:

$$m_e = \frac{1}{2}\left(\frac{n_2\cos\theta - [n^2 - \sin^2\theta]^{1/2}}{n_2\cos\theta + [n^2 - \sin^2\theta]^{1/2}}\right)^2 + \frac{1}{2}\left(\frac{\cos\theta - [n^2 - \sin^2\theta]^{1/2}}{\cos\theta + [n^2 - \sin^2\theta]^{1/2}}\right)^2.$$

13. A method as claimed in claim 1, wherein in step (g), according to the statistical method, the internal reflection coefficient ($m_i$) is defined as:

$$m_i = 1 - \left[\frac{(1-m_e)}{n^2}\right].$$

14. A process as claimed in claim 1, wherein in step (i), diffuse reflectance (R) is defined by the statistical method as:

$$R = \frac{(1 + r^2 - t^2) + [(1 + r^2 - t^2)^2 - 4r^2]^{1/2}}{2r},$$

where r and t are parameters.

15. A process as claimed in claim 14, wherein the Simplified particle model theory defines 'r' and 't' as:

$$r = t = \left(\frac{1-A}{2}\right),$$

wherein Absorbance $A$ is given by $A = \left[\frac{(1-m_e)(1-T)}{(1-m_iT)}\right],$ wherein $T = e^{-2\alpha d/3}$.

16. A process as claimed in claim 14, wherein the Modified particle model theory defines 'r' and 't' as:

$$r = \left(\frac{3m_e}{4}\right) + \frac{T}{2}[(1-m_e)(1-m_i)] \times \left\{\frac{1}{(1-m_iT)} - \frac{(1-m_i/2)(1-m_e/2)}{1+m_iT/2}\right\}, \text{ and}$$

$$t = \left(\frac{m_e}{4}\right) + \frac{T}{2}[(1-m_e)(1-m_i)] \times \left\{\frac{1}{(1-m_iT)} + \frac{(1-m_i/2)(1-m_e/2)}{1+m_iT/2}\right\}.$$

17. A process as claimed in claim 14, wherein the Parallel plane model defines 'r' and 't' as:

$$r = r_o + \left[\frac{(1-r_o)^2 r_o e^{-\alpha d}}{1 - r_o^2 e^{-2\alpha d}}\right], \text{ and}$$

$$t = \left[\frac{(1-r_o)^2 r_o e^{-\alpha d}}{1 - r_o^2 e^{-2\alpha d}}\right], \text{ wherein}$$

$$r_o = \left(\frac{1-n}{1+n}\right)^2.$$

18. A process as claimed in claim 14, wherein the Melamed theory defines 'r' and 't' as:

$$r = m_e + \frac{1}{2}\left\{\frac{(1-m_e)(1-m_i)M}{1-m_iM}\right\}, \text{ and}$$

$$t = \frac{1}{2}\left\{\frac{(1-m_e)(1-m_i)M}{1-m_iM}\right\}, \text{ wherein}$$

$$M = \frac{2}{(\alpha d)^2}[1 - (\alpha d + 1)e^{-\alpha d}].$$

19. A process as claimed in claim 1, wherein after obtaining the diffuse reflectance in step (i) by the statistical method, the user is provided with an opportunity to calculate the diffuse reflectance by the K-M method or to calculate the specular reflectance or to terminate the program.

20. A process as claimed in claim 1, wherein if the user doesn't make a proper choice at any stage, he is asked to make a proper choice or to terminate.

21. A method as claimed in claim 1, wherein the parameters obtained from the user and those calculated are stored in a file.

22. A method as claimed in claim 21, wherein the file is a new file or an already existing file.

23. A method as claimed in claim 1, wherein the method is used in infrared region.

24. A method as claimed in claim 23, wherein the method is used in the wavelength range of 0.8 $\mu$m to 1000 $\mu$m.

25. A method as claimed in claim 1, wherein the method is used in visible region.

26. A method as claimed in claim 25, wherein the method is used in the wavelength range of 400 nm to 800 nm.

27. A method as claimed in claim 1, wherein the method is used in UV region.

28. A method as claimed in claim 27, wherein the method is used in the wavelength range of 200 nm to 400 nm.

29. A method as claimed in claim 1, wherein the method is used for calculating specular and diffuse reflectance of solids selected from the group comprising of metals, non-metals, conductors, semiconductors, insulators and dielectrics and liquids selected from the group comprising of organic and inorganic liquids.

30. A method as claimed in claim 1, wherein the agreement between experimental and computed specular reflectance values is ±5%.

31. A method as claimed in claim 1, wherein the method is used for optical characterization of new materials.

32. A method as claimed in claim 1, wherein the method is used for development of required materials for fire proof materials.

33. A method as claimed in claim 1, wherein the method is used for development of required materials for energy saving process.

34. A method as claimed in claim 1, wherein the method is used for development of required materials for thermal insulation.

* * * * *